United States Patent [19]

Campbell et al.

[11] Patent Number: 5,405,606

[45] Date of Patent: Apr. 11, 1995

[54] EMBALMING COMPOSITION AND METHOD

[75] Inventors: James W. Campbell; John L. Margrave, both of Houston, Tex.

[73] Assignee: EFH, Inc., Houston, Tex.

[21] Appl. No.: 161,893

[22] Filed: Dec. 3, 1993

[51] Int. Cl.⁶ .............................................. A01N 1/00
[52] U.S. Cl. ........................................ 424/75; 424/3; 27/22.1; 27/22.2; 252/106; 514/717
[58] Field of Search .................. 424/75, 3; 27/22.1, 27/22.2; 252/106; 514/717

[56] References Cited

U.S. PATENT DOCUMENTS

| | | | |
|---|---|---|---|
| 3,057,775 | 10/1962 | Rendon | 424/75 |
| 3,197,366 | 7/1965 | Cannon et al. | 424/75 |
| 3,249,502 | 5/1966 | Hayden | 424/75 |
| 3,264,182 | 8/1966 | Langner | 424/75 |
| 3,293,127 | 12/1966 | Beck | 424/75 |
| 3,573,082 | 3/1971 | Fremling | 424/75 |
| 3,852,418 | 12/1974 | Tucker, Jr. | 424/75 |
| 3,912,809 | 10/1975 | Rendon | 27/22.2 |
| 4,021,537 | 5/1977 | Saurino | 424/54 |
| 4,121,944 | 10/1978 | VanLandingham | 424/75 |
| 4,263,278 | 4/1981 | Saurino et al. | 424/75 |
| 4,339,462 | 7/1982 | Muntwyler et al. | 252/106 |
| 4,404,181 | 9/1983 | Mauthner | 424/75 |
| 4,946,669 | 8/1990 | Siegfried et al. | 424/75 |
| 5,196,182 | 3/1993 | Ryan | 424/75 |
| 5,260,048 | 11/1993 | Ryan | 424/3 |

OTHER PUBLICATIONS

McKone, Harold T., "Embalming: A Rite Involving Early Chemistry", Todays Chemist at Work, Apr. 1994, pp. 68–70.

Wineski, Lawrence E. and Arthur E. English, "Phenoxyethanol as a Nontoxic Preservative in the Dissection Laboratory", Acta Anat 1989: 136:155–158.

Bedino, James H., "Millenium/New Era—Champion's Third Generation of Embalming Chemicals", Champion Report, (no date).

Carolina Carosafe, "Preserved Animals", (no date).

Connecticut Valley, "Preserved Material", (no date).

Nebraska Scientific, "Quality Specimens", (no date).

Streck Tissue Fixative, Streck Laboratories, Inc., Oct., 1992.

Ward's, "Preserved Materials", (no date).

Champion, "Millenium New Era Crisine Ultra Brochure and Material Safety Data Sheet" dated Oct., 1993.

Bedino, James H., "Expanding Encyclopedia of Mortuary Practices" No. 613, 1992, pp. 2466 through 2469.

Champion, "Millenium New Era Cavity 48 and Material Safety Data Sheet", dated Oct., 1993.

*Primary Examiner*—Thurman K. Page
*Assistant Examiner*—Amy Hulina

[57] ABSTRACT

An improved embalming composition and method has been developed. The embalming fluid is a mixture including glutaraldehyde, an aromatic ether of ethanol phenoxyethanol, at least one alcohol, and a polyhydric alcohol humectant. The formulation has no formaldehyde.

14 Claims, No Drawings

EMBALMING COMPOSITION AND METHOD

BACKGROUND OF THE INVENTION

Embalming fluids currently used contain significant quantities of formaldehyde. The formaldehyde embalming solutions are injected into the arteries and also introduced into the body cavity. Generally the cavity formulation is more concentrated because the naturally occurring fluids in the body cavity will dilute the formaldehyde formulation. The formaldehyde solutions also typically contain other additives such as humectants. Although formaldehyde solutions have been the embalming fluids of choice, there are a number of drawbacks. Formaldehyde is associated with certain health and environmental risks. In the United States, worker exposure to formaldehyde is subject to regulation. Also, formaldehyde can cause problems with the presentation of the body, because it dehydrates the tissue.

In U.S. Pat. No. 3,057,775 issued Oct. 9, 1962 to Randow entitled "Embalming Composition", glutaraldehyde was used instead of formaldehyde as a preservative in the embalming fluid. Glutaraldehyde was mixed with other preservatives in the formulations disclosed. If glutaraldehyde were used as the sole preservative, it would not be less than 7% of the solution. However, glutaraldehyde should be stabilized in the fluid to prevent oxidation and may polymerize in certain concentrations. Glutaraldehyde is tolerable to handle and does not have a noxious odor. Also, glutaraldehyde does not dehydrate tissue.

U.S. Pat. No. 3,912,809 issued on Oct. 14, 1975 to Randow entitled "Disinfecting Embalming Composition", discloses a fluid that is 2% by weight glutaraldehyde and an alkalizing agent to adjust the pH of the solution to pH 8~8.5. The glutaraldehyde is not stable in the alkalizing solution for more than a few weeks and the disclosure recognizes the problem of polymerization when glutaraldehyde is present in large concentrations. According to the patent, the shelf life problem is resolved by initially preparing two solutions. One is the glutaraldehyde solution which typically also includes formaldehyde and other is the alkalizing solution. The two solutions are mixed as needed. This composition is reported to significantly reduce the microbial growth in human remains.

The desire to eliminate exposure for formaldehyde has been examined by investigators involved in cadaver preservation. Wineski et al., "Phenoxyethanol as a Nontoxic Preservative in the Dissection Laboratory," *Acta Anat.* Vol. 136 pp. 155–158 (1989). The cadavers were embalmed by injection with about 24 liters of formaldehyde fluids. After embalming the cadavers were immersed or completely wrapped with cloth heavily soaked in phenoxyethanol. The exposure to phenoxyethanol is environmentally preferable to formaldehyde. However, the success of the technique depended on good initial preparation of the cadavers with a formaldehyde fluid.

A need exists for an embalming fluid that is safe to handle and is relatively simple to prepare for use. The fluid must achieve acceptable standards for presentation of the deceased. Previous alternatives to formaldehyde fluids have been solutions with stability problems associated with higher levels of glutaraldehyde or were cumbersome to use.

SUMMARY OF THE INVENTION

A new embalming fluid capable of use as an arterial and cavity fluid has been developed. The fluid is a mixture of glutaraldehyde, at least one aromatic ether of ethanol, at least one alcohol, and a humectant. The composition may be prepared as a concentrate or diluted with water to the desired concentration for immediate use by the embalmer. A more concentrated fluid can be used in the body cavity. The fluid may contain various additives conventionally used in embalming fluids, including a color additive, pH buffer, antioxidant, and perfume. A biocide may also be added for additional cidal activity in addition to the fluid components to kill bacteria, viruses or other microbes.

One preferred formulation of the present invention for arterial injection with a range of the components by volume after dilution is glutaraldehyde from about 0.5% to about 2.0%; aromatic ether of ethanol from about 1% to about 3%; a humectant of polyhydric alcohol or mixtures thereof from about 5% to about 9%; ethanol from about 27% to about 37%; and made up with water. The fluid used in the cavity will be on the higher side of the concentration ranges. A preferred aromatic ether of ethanol used with fluid is phenoxyethanol. The polyhydric alcohol component can be chosen from various chemicals including a mixtures of glycerol and 1-2 propanediol. Other components may be added to the fluid such as dimethylsulfoxide from about 0.5% to about 1% by volume of the fluid which acts as a penetrant. Also, ethoxyethanol from about 1% to about 2% may be included.

The fluid of the present invention provides improved results as compared to formaldehyde based fluids. In bodies embalmed with the fluid and method of this invention, discolorations such as hematomas visible in the skin of the deceased prior to embalming were lessened or eliminated. Also, the penetration into the tissue is superior as compared to other formaldehyde based fluids. The fluid does not contain formaldehyde which is a chemical currently regulated by federal exposure standards in the work place. The embalming fluid of the present invention is more pleasant to use because the odor is not as noxious and strong as the formaldehyde based solutions.

DETAILED DESCRIPTION OF THE INVENTION

The improved embalming fluid of the present invention is a unique mixture of glutaraldehyde, at least one aromatic ether of ethanol, at least one humectant, and at least one alcohol. Generally, the fluid is diluted with water prior to use. The fluid can be prepared in dilutions appropriate for arterial injection, as well as a more concentrated form for use in the body cavity.

The preferred formulation includes the following components by volume after dilution: glutaraldehyde from about 0.5% to about 2%, aromatic ether of ethanol from about 1% to about 3%, humectant from about 5% to about 9%, and an alcohol from about 27% to about 37%. A preferred humectant is a polyhydric alcohol or mixtures of more than one polyhydric alcohol. A preferred alcohol is ethanol. Other alcohols or mixtures of one or more may be used. A preferred aromatic ether of ethanol is phenoxyethanol. The preferred components are not intended to limit the scope of the inventions and alternative components within the scope of the invention will be recognized by those skilled in the art.

The following Example 1 is an illustration of the improved embalming composition for use in arterial injection.

| Components | Percent by Volume |
|---|---|
| Ethyl Alcohol | 28.5% |
| Glutaraldehyde | .5% |
| 1-2 Propanediol | 1.24% |
| Phenoxyethanol | 1.47% |
| Glycerol | 5% |

The rest of the volume is made up with water. In addition, ethoxyethanol in about 1.49% by volume may be added to Example 1. The fluid in Example 1 has been used in human remains. The composition preserved the body for at least seven to ten days.

In addition to the components in Example 1, a pH buffer and/or anti-oxidant may be included to maintain the stability of the glutaraldehyde. The pH buffer would adjust the pH in the range of pH~7 to pH~9. Also, a biocide may be added to further deter microbial growth. For instance, bactericide or a viricide may be included such as benzalkonium chloride or other quaternary ammonium compounds. In addition, other additives conventionally used in embalming fluids such as color additives or an odorant such as perfume may be included. It is not intended to limit the claimed formulation to exclude additives known to be used in embalming compositions that would be compatible with the formulation of the present invention.

A cavity fluid may be prepared according to Example 2.

| Components | Percent by Volume |
|---|---|
| Ethyl Alcohol | 35.63% |
| Glutaraldehyde | 1.13% |
| Phenoxyethanol | 2.45% |
| Glycerol | 5% |
| Ethoxyethanol | 1.5% |
| 1-2 Propanediol | 2.48% |

The fluid may also include dimethyl sulfoxide (DMSO) in about 0.5% to about 1% by volume of the fluid. The DMSO may be a more preferred additive to a cavity fluid.

The embalming method of the present invention utilizes the new fluid described above. Typically, the fluid is injected by arterial delivery into the subject and allowed to penetrate the tissue. The fluid and method of this invention exhibits excellent penetration and delivery characteristics as compared to formaldehyde based fluids. Also, discolorations caused by hematomas and other conditions were lessened when the deceased was embalmed using the improved fluid of the present invention. The improved fluid also relieves blood clots which can impair the preservation of the body. This is particularly important if the embalming process is delayed after death and blood clots form prior to injection of the fluid. The fluid of the present invention appears to break up the blood clots and improve delivery of the fluid through the arteries. The formaldehyde fluids do not exhibit alleviation of discoloration or break up blood clots as compared to the fluid and method of the improved embalming composition described herein.

Generally, the arterial fluid is made up of a less concentrated solution within the prescribed ranges. The cavity fluid is introduced into the central body cavity of the deceased and this fluid is generally more concentrated within the ranges. The glutaraldehyde component in the present fluid is a relatively small concentration at levels not susceptible to polymerization. Also, the improved fluid is stable and does not require multiple mixing steps with more than one solution. The same solution may be diluted as desired for use as an arterial or cavity fluid.

The examples and methods described herein are not intended to limit the scope of the invention. Those skilled in the art will recognize variations and substitutions in the composition and method that fall within the scope of the invention.

We claim:

1. An embalming fluid comprising
   glutaraldehyde in the amount of about 0.5% to about 2.0% by volume of the fluid;
   phenoxyethanol in the amount of about 1% to about 3% by volume of the fluid;
   alcohol in the amount of about 27% to about 37% by volume of fluid;
   at least one polyhydric alcohol in the amount of about 5% to about 9% by volume of the fluid; and
   water.

2. An embalming fluid of claim 1 wherein said polyhydric alcohol is selected from the group consisting of glycerol, 1-2 propanediol and mixtures thereof.

3. The embalming fluid of claim 1 additionally comprising a color additive.

4. The embalming fluid of claim 1 additionally composing a pH buffer.

5. The embalming fluid of claim 1 additionally comprising an antioxidant.

6. The embalming fluid of claim 1 additionally comprising a biocide.

7. The embalming fluid of claim 1 additionally comprising a perfume additive.

8. The embalming fluid of claim 1 additionally comprising dimethylsulfoxide from about 0.5% to about 1% by volume of the fluid.

9. The embalming fluid of claim 1 wherein said alcohol is ethanol.

10. The embalming fluid of claim 1 additionally comprising ethoxyethanol from about 1% to about 2%.

11. A method of embalming comprising:
    preparing a fluid according to claim 1; and
    introducing the fluid into a body.

12. The method of claim 11 wherein said introduction is arterial injection.

13. The method of claim 11 wherein said introduction is into the body cavity.

14. The method of embalming comprising the steps of injecting the fluid of claim 1 by arterial delivery; and delivering a more concentrated fluid of claim 1 than used in the arteries to the body cavity.

* * * * *